(12) United States Patent
Kodama et al.

(10) Patent No.: US 7,921,798 B2
(45) Date of Patent: Apr. 12, 2011

(54) OXYGEN DETECTOR SHEET AND OXYGEN DETECTING AGENT USING THE SAME, AND METHOD FOR MANUFACTURING OXYGEN DETECTOR SHEET

(75) Inventors: Ryuichi Kodama, Chiba (JP); Hiroshi Endo, Chiba (JP); Toshitaka Wada, Chiba (JP); Shigeru Tanaka, Chiba (JP)

(73) Assignee: Powdertech Co., Ltd., Kashiwa-shi (JP)

( * ) Notice: Subject to any disclaimer, the term of this patent is extended or adjusted under 35 U.S.C. 154(b) by 930 days.

(21) Appl. No.: 11/659,479

(22) PCT Filed: Jul. 26, 2005

(86) PCT No.: PCT/JP2005/013663
§ 371 (c)(1),
(2), (4) Date: Feb. 6, 2007

(87) PCT Pub. No.: WO2006/013754
PCT Pub. Date: Feb. 9, 2006

(65) Prior Publication Data
US 2009/0223432 A1 Sep. 10, 2009

(30) Foreign Application Priority Data
Aug. 6, 2004 (JP) .................................. 2004-230943

(51) Int. Cl.
*G01D 21/00* (2006.01)
*G01N 33/00* (2006.01)
(52) U.S. Cl. ........................................ 116/206; 436/136
(58) Field of Classification Search .................. 116/206, 116/DIG. 14; 436/904, 127, 136, 138
See application file for complete search history.

(56) References Cited

U.S. PATENT DOCUMENTS

| 4,526,752 | A | * | 7/1985 | Perlman et al. ................. 422/56 |
| 4,657,736 | A | * | 4/1987 | Marsoner et al. ............... 422/56 |
| 4,780,356 | A | * | 10/1988 | Otouma et al. ............ 428/32.37 |
| 5,053,339 | A | * | 10/1991 | Patel ................................ 436/2 |
| 6,139,935 | A | * | 10/2000 | Cullen et al. .................... 428/68 |
| 6,228,804 | B1 | * | 5/2001 | Nakashima ................... 503/226 |
| 7,472,667 | B2 | * | 1/2009 | Mochizuki et al. ........... 116/206 |
| 7,553,355 | B2 | * | 6/2009 | Torres et al. ................. 96/117.5 |
| 2006/0141106 | A1 | * | 6/2006 | Kodama et al. ............... 426/231 |

FOREIGN PATENT DOCUMENTS

| JP | 57 010451 A | 1/1982 |
| JP | 59-142463 A | 8/1984 |
| JP | 61-144568 A | 7/1986 |
| JP | 5-34332 A | 2/1993 |
| JP | 5-85623 U | 11/1993 |
| JP | 2644377 B2 | 5/1997 |

(Continued)

*Primary Examiner* — Amy Cohen Johnson
(74) *Attorney, Agent, or Firm* — Sughrue Mion, PLLC

(57) ABSTRACT

The oxygen detecting device (10) of the present invention includes an oxygen detector sheet having a sheet carrier (13) having a porous inorganic material filled therein which has been impregnated with an oxygen detecting fluid, and a film (11) having a predetermined oxygen transmittance for covering and sealing the sheet carrier (13). Since the sheet having the porous inorganic material filled therein is adopted, the oxygen detecting device has an excellent light resistance, leading to clear recognition of coloration for a long period of time. Because of excellent light resistance, the device keeps excellent property even after long exposure to a fluorescent lamp in a display case for displaying foods. Thus the device is suitable for checking quality of commercial products.

4 Claims, 5 Drawing Sheets

FOREIGN PATENT DOCUMENTS

| | | |
|---|---|---|
| JP | 9-318614 A | 12/1997 |
| JP | 10-148685 A | 6/1998 |
| JP | 11-190729 A | 7/1999 |
| JP | 11-192800 A | 7/1999 |
| JP | 11-276888 A | 10/1999 |
| JP | 2000-039429 A | 2/2000 |
| JP | 2000-072977 A | 3/2000 |
| JP | 2000-111541 A | 4/2000 |
| JP | 2000-214155 A | 8/2000 |
| JP | 2000-342235 A | 12/2000 |
| JP | 2002-308342 A | 10/2002 |
| JP | 2003-28850 A | 1/2003 |
| JP | 2003-149224 A | 5/2003 |
| JP | 2003-227797 A | 8/2003 |
| JP | 2003-322648 A | 11/2003 |

\* cited by examiner

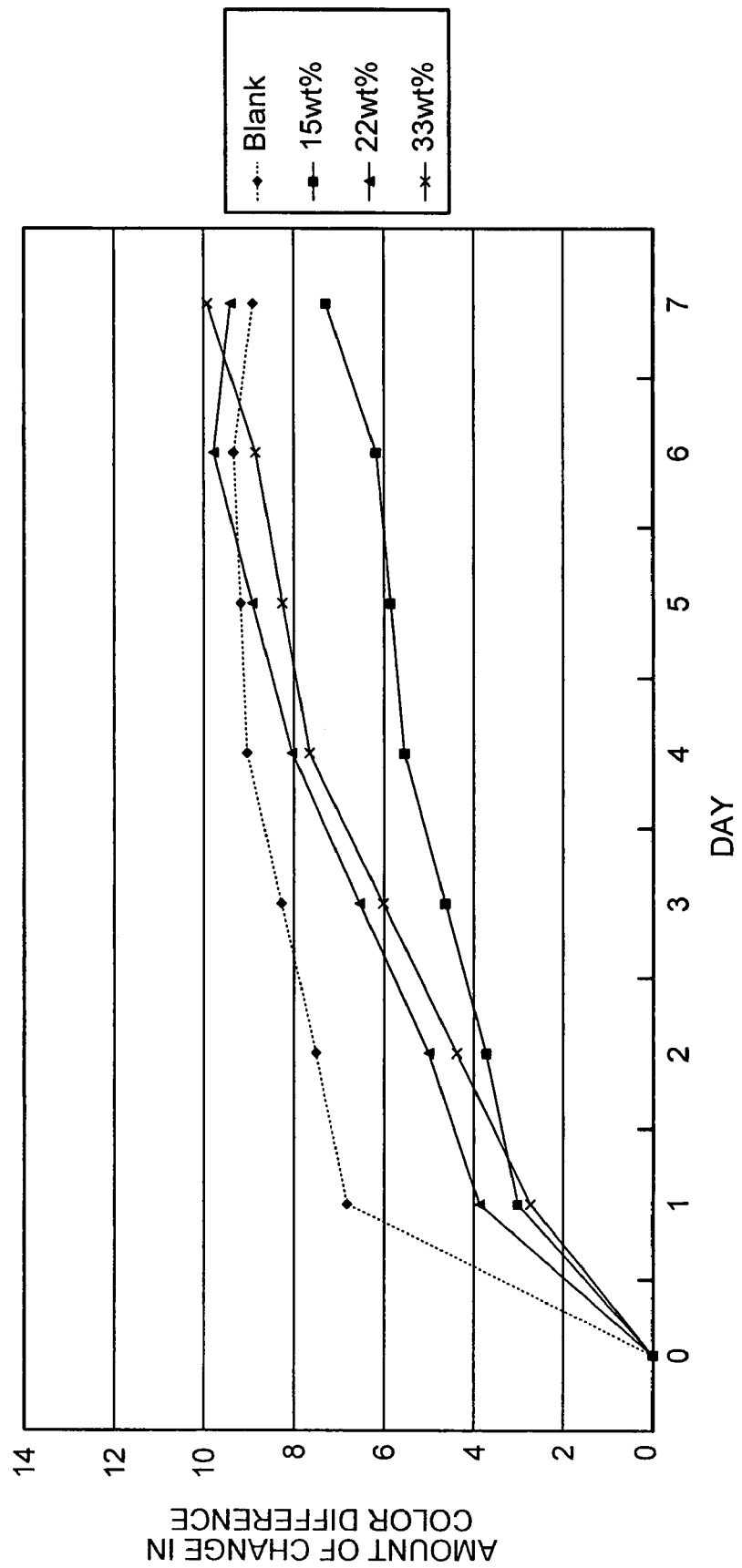

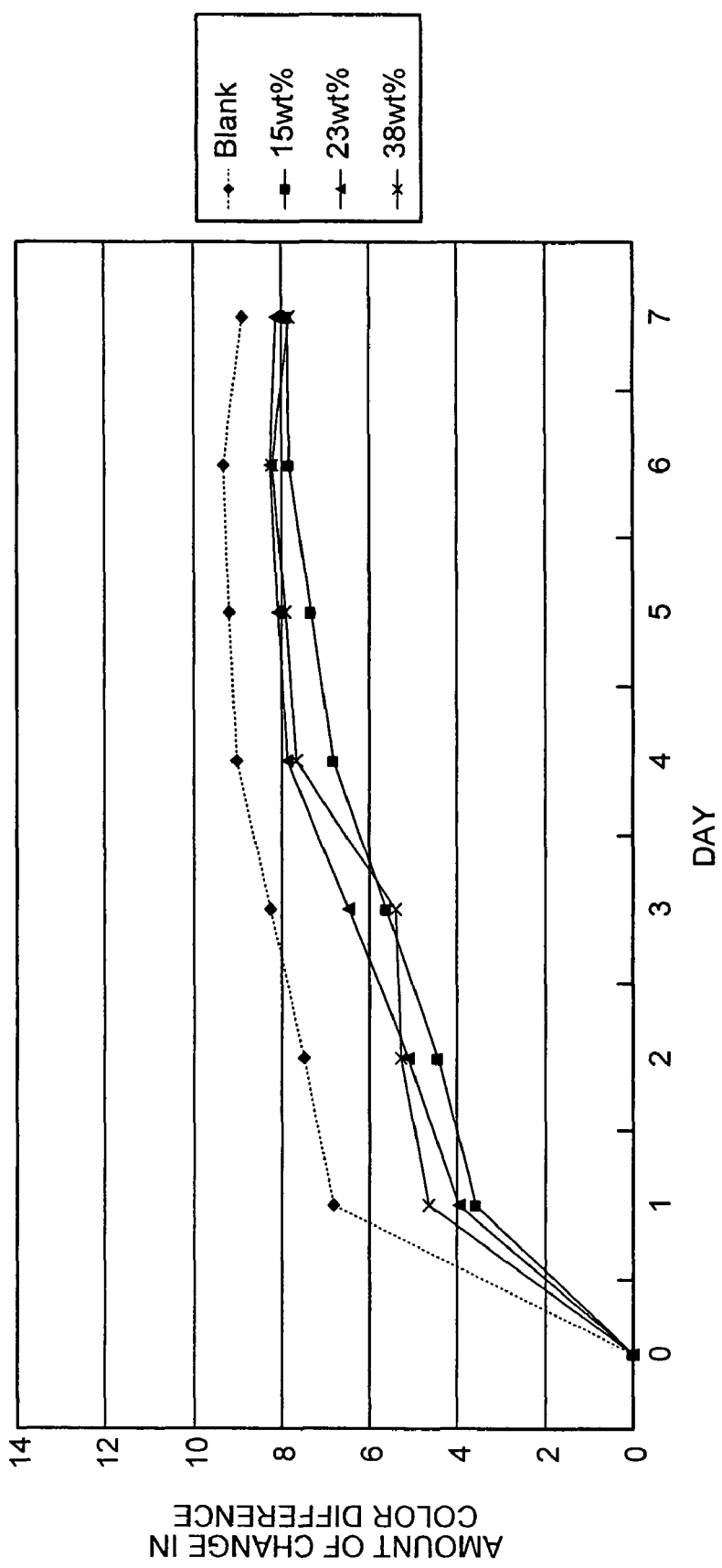

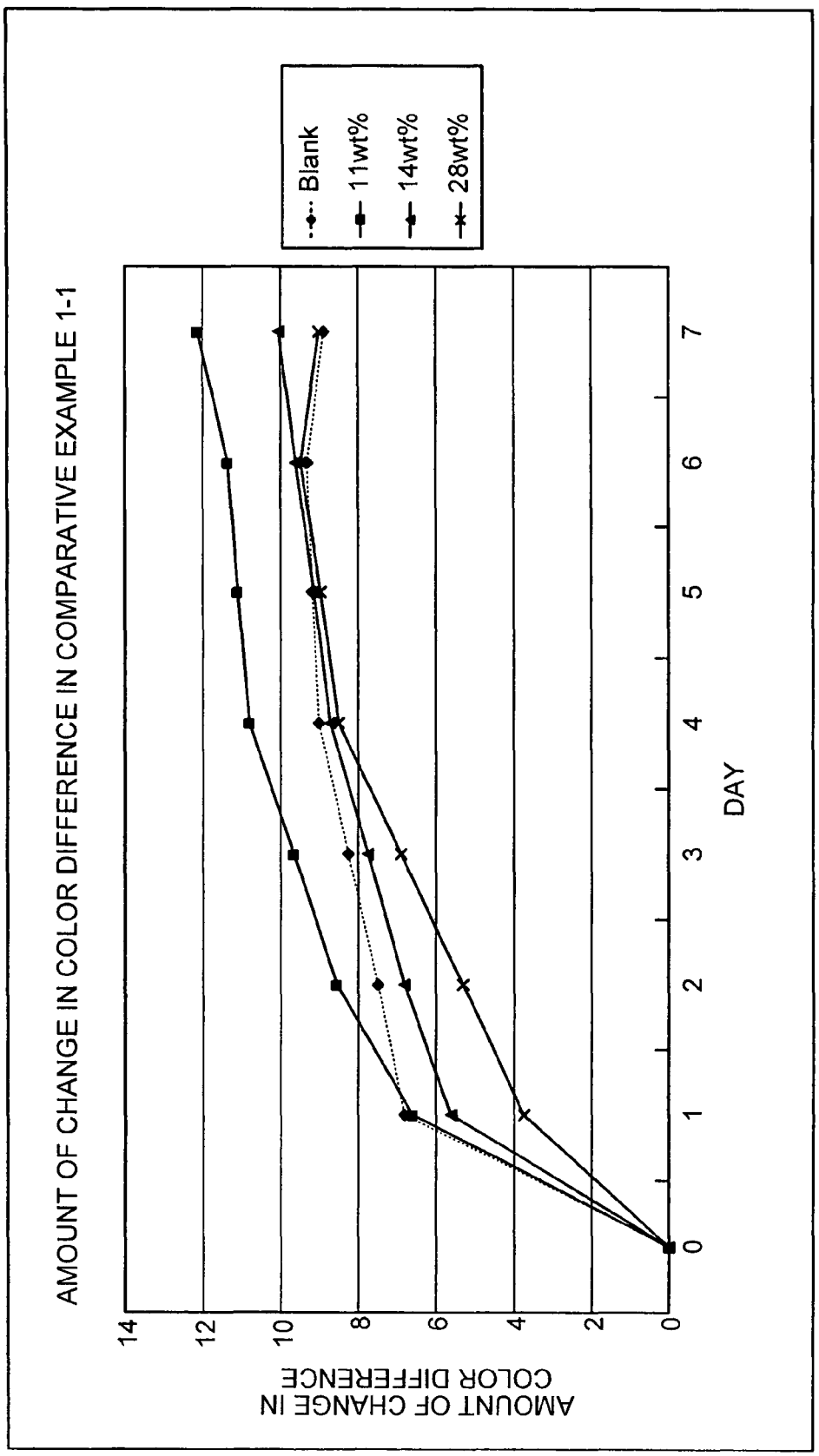

US 7,921,798 B2

OXYGEN DETECTOR SHEET AND OXYGEN DETECTING AGENT USING THE SAME, AND METHOD FOR MANUFACTURING OXYGEN DETECTOR SHEET

TECHNICAL FIELD

The present invention relates to an oxygen detector sheet excellent in light resistance and allowing management of the freshness of a food such as a packaged food with gas replacement and a packaged food with deoxidation, an oxygen detecting device using the same, and a method for manufacturing the oxygen detector sheet.

BACKGROUND ART

Conventionally, oxygen detecting devices have been used in a variety of fields of, e.g., food; printing ink; electrics, mechanics, and appliances; and medicaments and medical products, for determining quality preservation and for controlling quality of various products contained in a packaging container, the products including food; inks; electrics, mechanics, and appliances; medicines; and medical products.

For example, in the field of food, the oxygen detecting device mainly targets at foods to be preserved for a long period of time. In order to prevent deterioration due to oxidation of oils and vitamins contained in food, damages caused by insects, changes in color and gloss, and growth of mold or bacteria, the oxygen detecting device is enclosed chiefly with a deoxidizer (oxygen absorbent) in a gas-impermeable hermetically-sealed package bag containing such foods. In the package bag, the state is kept where there is substantially no oxygen for a long period of time. Irrespectively of the type of food, upon detection of a predetermined amount of oxygen entering the package bag from outside, the color of the oxygen detecting device changes uniformly.

That is, conventionally, a food, a deoxidizer, and an oxygen detecting device are enclosed together in the package bag, and the deoxidizer absorbs or reacts with oxygen entering the package bag from outside through the package bag, an enclosing seal portion, a pin hole on the package bag, etc. with a lapse of a long period of time during food preservation, to thereby reduce or remove oxygen in the package bag. The amount of oxygen remaining in the package bag (that is not absorbed to the deoxidizer or reacted with the deoxidizer) due to a reduction in performance of the deoxidizer or other factors is checked based on the presence or absence of a color change of the oxygen detecting device, which is used as an index for visually determining the degree of freshness of the packaged food (see, e.g., Patent Documents 1 to 6).

Patent Document 1: Japanese Patent Application Laid-Open Publication No. 2002-308342 A
Patent Document 2: Japanese Patent Application Laid-Open Publication No. 2000-342235 A
Patent Document 3: Japanese Patent Application Laid-Open Publication No. 2000-039429 A
Patent Document 4: Japanese Patent Application Laid-Open Publication No. H11-276888 A
Patent Document 5: Japanese Patent Application Laid-Open Publication No. H11-190729 A
Patent Document 6: Japanese Utility Model Application Laid-Open Publication No. H5-85623 A

DISCLOSURE OF INVENTION

Problem to Solved by the Invention

However, the oxygen detecting device in a food display case deteriorates with the lapse of time due to light emitted from a fluorescent lamp, bactericidal lamp, or the like, and therefore there is a problem of being unable to maintain appropriate color change.

In view of the problem above, an object of the present invention is to provide an oxygen detector sheet with excellent light resistance, an oxygen detecting device using the same, and a method for manufacturing such an oxygen detector sheet.

Means for Solving Problem

In order to solve the aforementioned problem, the first invention according to the present invention is an oxygen detector sheet comprising: a sheet carrier having a porous inorganic material filled therein, the porous inorganic material giving light resistance to the sheet carrier; and an oxygen detecting fluid carried in the carrier, wherein the content of the filled inorganic material in the sheet carrier is 15 to 38 percent by weight.

The second invention is the oxygen detector sheet according to the first invention, wherein the porous inorganic material for giving light resistance is silica.

The third invention is the oxygen detector sheet according to the second invention, wherein the silica is an amorphous silica.

The fourth invention is an oxygen detecting device comprising: a film having a predetermined oxygen transmittance; and the oxygen detector sheet according to any one of the first to the third inventions covered and sealed with the film.

The fifth invention is a method for manufacturing the oxygen detector sheet of the first invention, the method comprising: producing a paper while adding a light-resistant porous inorganic material thereto so that the material is held in the paper at the filling ratio of 15 to 38 percent by weight, the porous inorganic material giving light resistance to the sheet carrier; subsequently impregnating the sheet carrier with an oxygen detecting fluid; and drying the sheet carrier.

EFFECT OF THE INVENTION

According to the present invention, an oxygen detector sheet excellent in light resistance can be obtained. With this oxygen detector sheet covered and sealed with a film, an oxygen detecting device excellent in light resistance can be obtained.

BRIEF DESCRIPTION OF DRAWINGS

FIG. 4 is a graph that depicts a ratio of change in color difference in Test Example 1-1.
FIG. 5 is a graph that depicts a ratio of change in color difference in Test Example 1-2.
FIG. 6 is a graph that depicts a ratio of change in color difference in Comparative Example 1-1.

EXPLANATIONS OF LETTERS OR NUMERALS

| | |
|---|---|
| 10 | oxygen detecting device |
| 11 | film |

| | |
|---|---|
| 12 | window |
| 13 | oxygen detector sheet |

BEST MODE FOR CARRYING OUT THE INVENTION

The present invention will be explained in detail with reference to the drawings, although the present invention is not restricted to the following embodiments. Components constituting the following embodiments may include those that can be easily assumed by a person skilled in the art or those substantially identical thereto.

Embodiments

The oxygen detector sheet according to the following embodiments of the present invention has a sheet carrier having a porous inorganic material filled therein, and an oxygen detecting fluid carried in the carrier.

The content of the filled porous inorganic material is preferably in a range of, for example, 5 weight percent to 50 weight percent, suitably in a range of 10 weight percent to 30 weight percent. This is because light resistance is not excellent when the content is less than 5 weight percent and more than 50 weight percent.

Examples of the porous inorganic material may include oxides of silicon (Si), aluminum (Al), magnesium (Mg), calcium (Ca), zinc (Zn), barium (Ba), potassium (K) and others, mixtures thereof, and compound oxides containing any of these elements (for example, calcium silicate).

More specific examples of the porous inorganic oxides may include silica gel, silica (silicon dioxide), zeolite, mordenite, bentonite, montmorillonite, (activated) alumina, magnesia, titania, activated white earth, clay, slag, bauxite, porous glass beads.

Of these porous members, silica, silica gel, alumina, zeolite, and mordenite are preferable in view of light resistance of the resulting oxygen detecting device, visibility of color change, safety, etc. Each of these porous members may be used solely or in combination of two or more.

Silica ($SiO_2$) mentioned above may be natural or synthesized, and may be amorphous silica or crystalline silica.

With such filling of the porous inorganic material at the time of papermaking, the resulting oxygen detecting device can maintain its color in a good state after color change, which is particularly preferable in a use where light resistance is required, such as the use as an oxygen detecting device for monitoring quality of meat that is displayed for several days in a bright display case.

Figure 1:
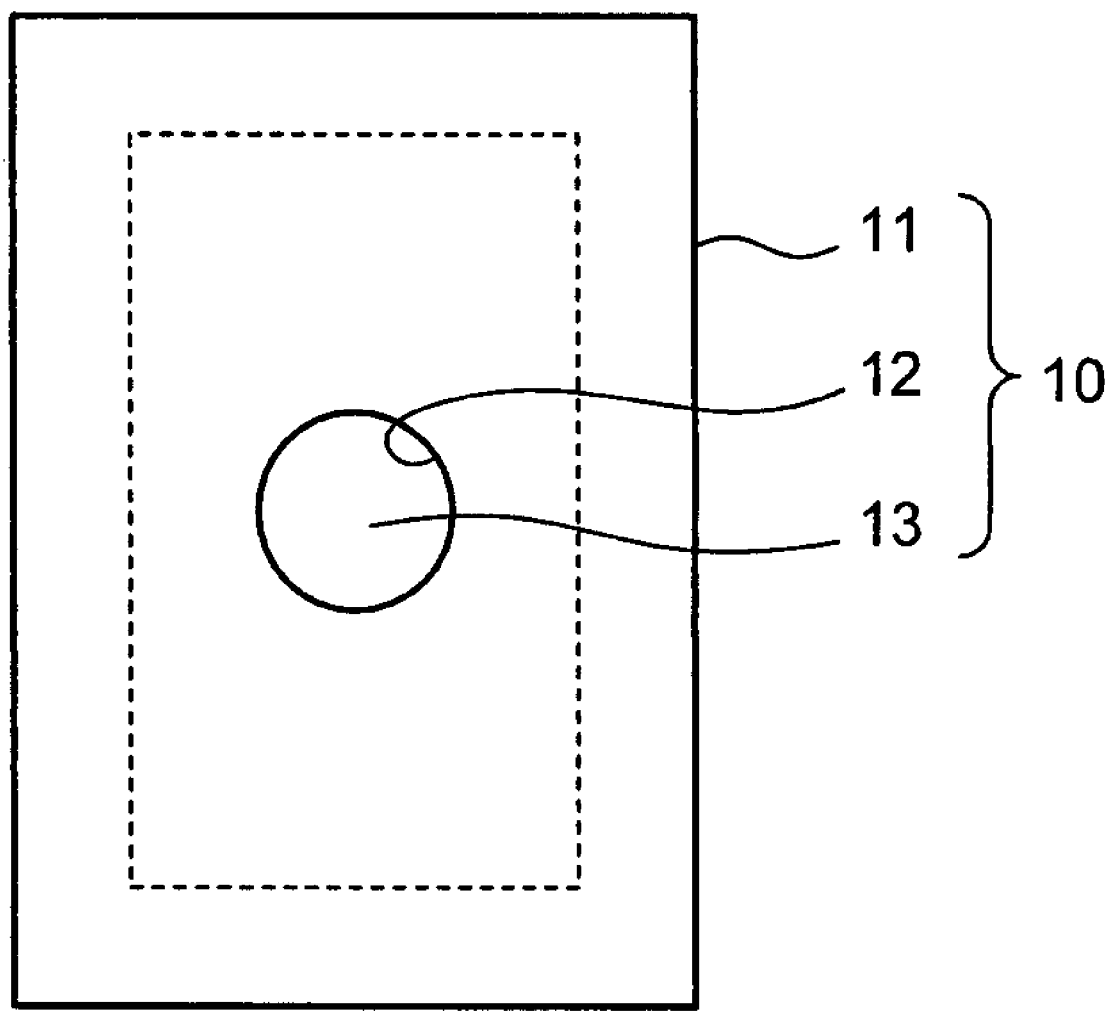
FIG. 1 is a schematic view of an oxygen detecting device.

An example of the oxygen detecting device according to the present embodiment is depicted in FIG. 1.

As depicted in FIG. 1, an oxygen detecting device 10 is composed of an oxygen detector sheet 13 with a sheet carrier containing a porous inorganic material filled therein which has been impregnated with a detecting solution, and a film 11 having a predetermined oxygen transmittance for covering and sealing the oxygen detector sheet 13. In order to ensure visibility of color, the entire film is made opaque, with a circular window 12 provided at one part. The shape of the window is not restricted to a circle.

The film 11 preferably has either one or both of a predetermined oxygen transmittance and carbon dioxide transmittance, particularly oxygen transmittance, according to the type of articles (e.g., food) to be under quality control and according to quality control conditions, such as storage temperature and humidity, replacement gas type and gas replacement ratio, and the degree of desired freshness of food.

The film may have an adhesive layer or double-faced tape on, e.g., the back surface of the film, so as to be easily attached or fixed to a desired counterpart surface.

One example of manufacturing of an oxygen detector sheet according to the present embodiment will be explained.

First, a detector sheet is produced by a papermaking process in which a porous inorganic material is filled in the sheet. The detector sheet is used as a sheet carrier. Next, the sheet carrier is immersed in a container containing an oxygen detecting solution. After immersion for a predetermined period of time, the sheet carrier is pulled up so that the oxygen detecting solution is squeezed out thereof, and is then dried to obtain an oxygen detector sheet.

Thereafter, the oxygen detector sheet is cut out to have a predetermined size, and is covered and sealed with a film, thereby forming an oxygen detecting device.

This oxygen detector sheet can detect the oxygen concentration or the presence or absence of oxygen inside or outside the package container for food or the like and the oxygen concentration or the presence or absence of oxygen transmitting or penetrating through the film. In particular, it is possible to detect the fact that oxygen has been sufficiently removed through gas replacement at the time of gas-replace packaging or deoxidation packaging, or the fact that the oxygen concentration is at a limited amount. Through a change in color, that is, a change in hue, tint, or brightness, the oxygen concentration, the presence or absence of oxygen, etc. are displayed. With the porous inorganic material filled therein, excellent light resistance can be achieved.

Any conventionally-known film (oxygen transmittance control film) can be appropriately used in combination according to the type of the article and the quality control conditions.

As the detecting solution with which the sheet carrier is impregnated, any of conventionally-known solutions can be used, but a so-called oxidation-reduction type is preferably used. A typical example of an oxidation reduction-type oxygen detecting agent may be a combination of a specific coloring agent, such as methylene blue, and a reducing agent for reducing the coloring agent, such as glucose (see, e.g., Japanese Patent Application Laid-Open Publication No. 2000-39429, Japanese Patent Application Laid-Open Publication No. S53-120493, Japanese Patent Application Laid-Open Publication No. S56-60349). This combination utilizes a phenomenon such that, when oxygen is present, methylene blue itself is oxidized to show a blue color, but when no oxygen is present, the coloring agent showing the blue color is reduced by the reducing agent, such as glucose (oxygen that has oxidized the coloring agent is removed by glucose and glucose itself is then oxidized), to become colorless. Normally, a coloring agent. (for example, a reddish coloring agent, such as a red food coloring), is mixed in order to clearly emphasize the fact that methylene blue has become colorless.

Figure 2:
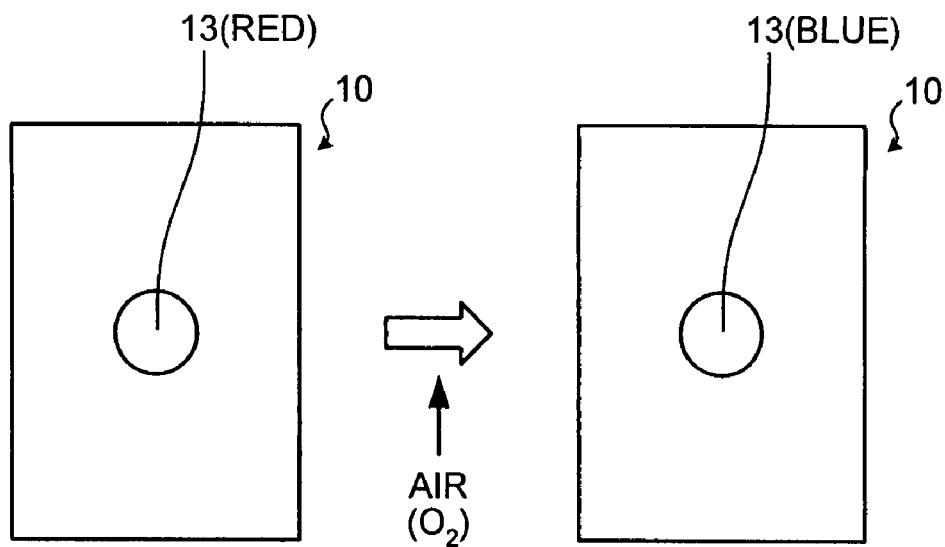
FIG. 2 is a view of an example of a color change of the oxygen detecting device.

That is, as depicted in FIG. 2, the color of the detecting sheet 13 of the oxygen detecting device 10 is red in an initial state. The color changes to blue when oxygen is absorbed with the lapse of time, whereby the index of freshness is checked.

For example, when the oxygen detector sheet, i.e. a member that constitutes the oxygen detecting device, is formed by impregnating a base material containing a red coloring agent with methylene blue, the color changes from red to blue as the surrounding oxygen concentration is increased to have a value equal to or greater than 0.3.

Examples of the oxygen transmittance control film (the film) may include transparent films, such as polyethylene, polypropylene, polyester, polyamide, polycarbonate, cellulose acetate, and cellophane. These films may be elongated as long as they are transparent, and may have metal deposited on its surface. These films may be laminated in an arbitrary combination.

In particular, when the subject food is a prepared food or a packed meal containing prepared foods, a film having oxygen transmittance (oxygen transmittance) of 1000 to 3000 ml/m$^2$·24 hrs·atm, preferably, 1500 to 2500 ml/m$^2$·24 hrs·atm can be adopted as the film for covering and sealing the oxygen detector sheet (oxygen transmittance control film).

Preferably, the oxygen transmittance control film may have a resistance (insolubility) against moisture (broth), edible oil, alcohol, alcohols, etc. in the accommodated food. Examples of such a film may include a polypropylene (OP)/polyethylene (PE) laminated film and a polyester (PET)/polyethylene (PE).

When the oxygen transmittance control film having such an oxygen transmittance is used to cover and enclose the oxygen detector sheet after a lapse of predetermined days (for example, 2 to 3 days after manufacturing of the food) under room temperature (for example, temperatures around 15 degrees Celsius to 25 degrees Celsius), which are temperatures inside a display case for prepared foods in a supermarket, the color of the oxygen detector sheet can change from red to blue. With this, the degree of freshness (quality preservation period) of the prepared food and the packed meal containing prepared foods can be easily and reliably determined.

Examples of foods whose freshness is controlled under a temperature condition near the room temperature for a short period of time in a similar manner to the prepared food and the packed meal containing the prepared foods may include Japanese confectioneries and western confectioneries. In addition, dried fruits, grain foods, etc. can also be under the freshness control by setting appropriate conditions.

(Freshness Control Over Foods, Such as Raw Animal Meat)

When the subject food is raw animal meat, the oxygen detecting device may be enclosed with small sub-packages of raw animal meat in a hermetic mantle package bag. If necessary, a deoxidizer may also be enclosed in this exterior package bag. In this mantle package bag, gas replacement may be performed with carbon dioxide ($CO_2$) so that the oxygen gas concentration immediately after gas replacement is normally equal to or smaller than 0.05% and often approximately 0.001% to 0.05%, and the package bag may then be transported and stored at approximately 0 degree Celsius for several tens of days (for example, 40 days) (embodiment A).

As for the raw animal meat, the oxygen detecting device may be enclosed with small sub-packages of raw animal meat in a hermetic mantle package bag. If necessary, a deoxidizer may also be enclosed in this exterior package bag. The inside of the mantle package bag is then deaerated, and the package bag may be preserved in a frozen state for a long period of time or transported in a frozen state at a temperature at which quality deterioration hardly occurs (for example, −40 degrees Celsius to −18 degrees Celsius) (embodiment B).

After the raw animal meat is transported or stored under these various conditions (embodiment A or B), the hermetic mantle package bag may be opened and removed, and the content may be then arranged, e.g., a food display case (room) in a supermarket. As a result, the oxygen detecting device enclosed with the small packs is directly exposed to air. The oxygen detecting device starts absorbing ambient (atmospheric) oxygen, which passes and penetrates through the oxygen transmittance control film with a lapse of a predetermined days (for example: at temperatures from approximately 2 degrees Celsius to 10 degrees Celsius for 3 to 4 days). The oxygen detector sheet then detects that the concentration of oxygen entering the inside (oxygen detector sheet side) has a predetermined value. Upon detection, the color of the detecting agent can change from red to blue. With this, the degree of freshness of the raw meat (quality preservation period) can be easily and reliably determined.

As a film (oxygen transmittance control film) covering and sealing the oxygen detector sheet for use at this time, a film having an oxygen transmittance degree (oxygen transmittance) of 1 to 50 ml/m$^2$·24 hrs·atm, preferably 5 to 20 ml/m$^2$·24 hrs·atm can be adopted.

Examples of such an oxygen transmittance control film may include a polyethylene terephthalate (PET)/polyacryl nitrile (PAN) laminated film and a polyvinyl chloride-coated polyethylene film (KNY/PE).

With the oxygen detecting device coated and sealed with the film having such a degree of oxygen transmittance, even if the oxygen detecting device has been attached to the external surface of the small pack at the stage of transportation or storage after packing the raw animal meat or has been even enclosed in a breathable small pack, the oxygen detecting device is further accommodated in the mantle package bag together with the small packages of raw animal meat during the period of transportation and storage under the low-oxygen state. Therefore, the small-packed raw meat hardly deteriorates in quality, and thus the oxygen detecting device is kept without changing its color during that period, indicating that the raw meat is fresh.

However, in the present invention, once the mantle package bag which has maintained the low-oxygen state is opened to expose the oxygen detecting device to air, with a lapse of the days (3 days to 4 days) at 2 degrees Celsius to 10 degrees Celsius (for example, 6 degrees Celsius), a predetermined amount of oxygen in air may be absorbed to change the color of the oxygen detector sheet from red to blue.

In this manner, either one or both of the oxygen transmittance and carbon dioxide transmittance, particularly oxygen transmittance, of the film covering the oxygen detector sheet may be adjusted to a predetermined value according to the type of article (such as food) to be under quality control and according to quality control conditions, such as storage temperature and humidity, replacement gas type and gas replacement ratio, and the degree of freshness, whereby the color change criteria of the oxygen detecting device may be altered. With this, the degree of freshness (quality preservation period) of raw animal meat can be easily and reliably determined.

Examples of other foods with their freshness controllable in a manner similar to that for raw animal meat may include fishery products (also collectively called fish), such as shrimps, crabs, oysters, and fish.

In the aforementioned explanation, explanation has been made referring to preferred embodiments in which a film having a degree of oxygen transmittance (oxygen transmittance) of 1000 to 3000 ml/m$^2$·24 hrs·atm, preferably 1500 to 2500 ml/m$^2$·24 hrs·atm, is used as the film (oxygen transmittance control film) covering and sealing the oxygen detector sheet for freshness control of prepared food and a packed meal containing prepared foods and in which a film having a degree of oxygen transmittance (oxygen transmittance) of 1 to 50 ml/m$^2$·24 hrs·atm, preferably 5 to 20 ml/m$^2$·24 hrs·atm, is used as the oxygen transmittance control film for freshness control of raw animal meat. However, the present invention is not restricted to these embodiments. For example, with any publicly-known film having either or both of various oxygen transmittances and carbon dioxide transmittances (See, e.g., "*Shokuhin Housou Binran* (Food packaging handbook)" p. 495, Table 2) covering and sealing the oxygen detector sheet, quality control over various subjects can be performed under various conditions.

In the present invention, the articles which are subjected to the quality control are not restricted to the aforementioned foods. Other examples of the articles may include foods whose taste, aroma, and flavor deteriorate due to oxidation degradation, such as dried noodles, glutens, spices, and confectioneries; articles of taste whose taste deteriorates due to oxidation degradation, such as cigarettes; medical products whose quality in medicinal properties and medical effects largely depend on the preservation period and temperature, such as medicaments, particularly viable cells (for example, lactic acid bacteria and vaccine), blood products, and medicaments containing herbal medicines; emulsion and other cosmetics containing natural ingredients, etc. whose aroma, color, effect of making the skin beautiful, etc. tend to be lost due to oxidation degradation; articles whose quality and effects largely depend on the preservation period, temperature, oxidation degradation, and other factors, such as contact lenses, and their cleaning fluids and preservation fluids; and components and products which is required to have anti-corrosion property in view of function maintenance and aesthetic purposes, such as clock and electronic components, precision machines and instruments, costume jewelries, and decorative arts.

EXAMPLES

The present invention is further specifically explained hereinbelow referring to examples. However, the present invention is not restricted by these examples at all.

<Manufacturing of the Detecting Sheet>

A predetermined amount of a beaten pulp and amorphous silica (TOKUSIL GU-N (product name) from Tokuyama Corporation) which is a porous inorganic material were weighed and macerated at a 2 percent concentration, and then papermaking was performed aiming at a paper weight per square meter of 186 g/m². Then, the resultant product was pressured with an oil hydraulic press machine to 2.5 kg/cm², dehydrated, and then dried at 105 degrees Celsius to form a sheet carrier having amorphous silica filled therein. This sheet carrier was burnt and incinerated at 900 degrees Celsius for two hours, and its ash ($SiO_2$) was measured as 15.1 weight percent.

<Oxygen Detecting Solution>

13 parts by weight of 0.5% methylene blue aqueous solution, 13 parts by weight of 0.25% safranine T aqueous solution, 65 parts by weight of 30% glucose, and 9 parts by weight of 15% potassium hydroxide were mixed together to produce an oxygen detecting solution.

The sheet carrier was impregnated with the oxygen detecting solution for a predetermined time, and was then dried at 35 degrees Celsius for 30 minutes to formulate an oxygen detector sheet. Then, the resultant product was covered and sealed with a polyethylene terephthalate (PET)/polyacryl nitrile (PAN) laminated film to produce an oxygen detecting device.

Figure 3:
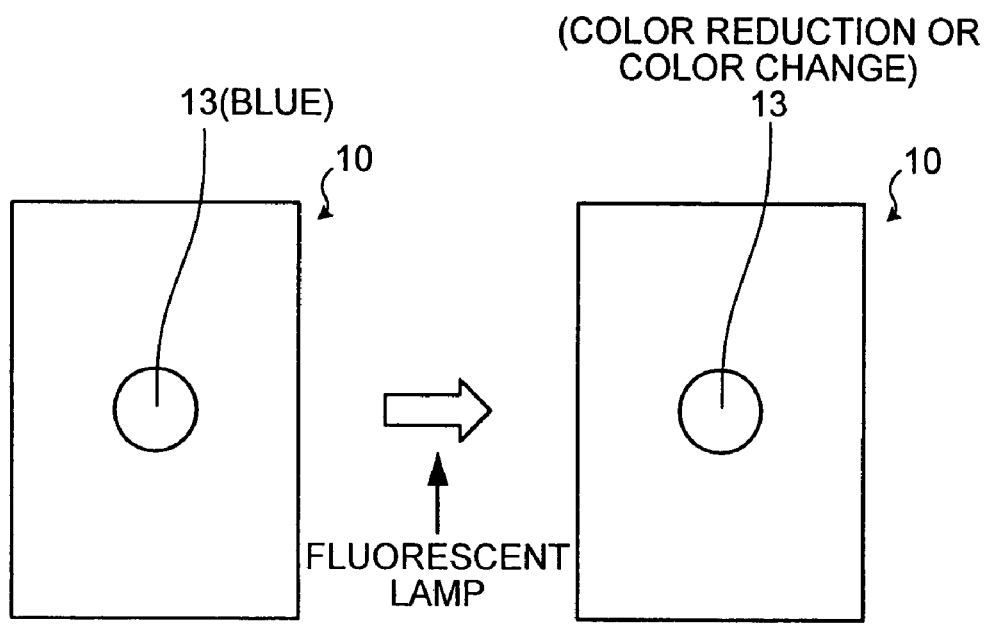
FIG. 3 is a view of color reduction or color change of an example of the oxygen detecting device.

As depicted in FIG. 3, the oxygen detecting device 10 thus formulated was exposed to air to change its color to blue. This oxygen detecting device 10 whose color has changed to blue was used under the condition at 6 degrees Celsius so as to be radiated with light of 1000 lux by using a fluorescent lamp. In this state, the presence or absence of color reduction or color change was checked by naked eyes every day.

For comparison, a material without addition of amorphous silica was subjected to the same manipulation.

The results are depicted in the following "Table 1". In the table, G represents no color change, M represents a color reduction, and B represents a significant color change or color reduction.

TABLE 1

|  | 1ST DAY | 2ND DAY | 3RD DAY | 4TH DAY | 5TH DAY | 6TH DAY |
|---|---|---|---|---|---|---|
| EXAMPLE | G | G | G | G | G | G |
| COMPARATIVE EXAMPLE | G | G | M | B | B | B |

As depicted in "Table 1", the color of the present example was not changed or reduced even after a lapse of 6 days. However, it was observed that the color of the comparative example was reduced after a lapse of approximately 3 days and the color change further proceeded on and after the fourth day.

Test Example 1

Subsequently, the addition amount of silica, i.e. the porous inorganic material, was studied.

In this Test Example, three types of silica were used. In Test Example 1-1, amorphous silica identical with the aforementioned example ("TOKUSIL GU-N" (product name) from Tokuyama Corporation) was used. In Test Example 1-2, "Fluorite R" (product name) from Tokuyama Corporation was used as calcium silicate. In Comparative Example 1-1, "Solex CM" (product name) from Tokuyama Corporation that is present as a mixture of $SiO_2$ and CaO was used.

Physical property values and compositions of these examples are depicted in the following Table 2.

TABLE 2

|  | TEST EXAMPLE 1-1 | TEST EXAMPLE 1-2 | COMPARATIVE EXAMPLE 1-1 |
|---|---|---|---|
| APPARENT RELATIVE DENSITY (g/cc) | 0.19 | 0.1 | 0.28 |
| AVERAGE PARTICLE DIAMETER (μm) | 13 | 25 | 14 |
| SPECIFIC SURFACE AREA (m²/g) | 220 | 120 | 70 |
| OIL ABSORPTION AMOUNT (c/100 g) | 200 | 450 | 130 |
| pH | 6.5 | 9.2 | 9 |
| $SiO_2$ (%) | 94 | 60 | 59 |
| CaO (%) | 0.02 | 24 (COMPOUND) | 21 (MIXTURE) |
| $Al_2O_3$ (%) | 0.6 | 0.5 | 0.4 |
| $Na_2O$ (%) | 0.3 | 0.4 | 0.3 |

At the time of papermaking, each silica was added at the ratio of 20 weight percent, 30 weight percent, and 50 weight percent, and operation was performed in the same manner as that in the aforementioned example to formulate oxygen detecting devices.

The amount of the additive represents a value of silica added before papermaking, whilst an inner filling amount represents a value of silica actually contained in the oxygen detecting device counting out the amount of silica flowing out during papermaking. Their relationships are depicted in "Table 3".

TABLE 3

| POROUS INORGANIC MATERIAL | ADDITIVE (wt %) | INTERNAL FILLING AMOUNT (wt %) |
|---|---|---|
| TEST EXAMPLE 1-1 | 20 | 15 |
|  | 30 | 22 |
|  | 50 | 33 |
| TEST EXAMPLE 1-2 | 20 | 15 |
|  | 30 | 23 |
|  | 50 | 38 |
| COMPARATIVE EXAMPLE 1-1 | 20 | 11 |
|  | 30 | 14 |
|  | 50 | 28 |

The oxygen detecting device thus produced was exposed to air to change its color to blue. By using this oxygen detecting device whose color has changed to blue, color reduction and color change were checked.

In light resistance test, a color difference was measured per day with and without irradiation of light of 1000 lux under an environment at 25 degrees Celsius. For color difference measurement, a calorimetric color difference meter "ZE2000" (product name) from Nippon Denshoku Industries Co., Ltd. was used to measure the color difference (ΔE*ab).

As for the results, the amounts of change of the respective Test Examples with reference to 0-th day are depicted in FIGS. 4 to 6.

FIG. 4 depicts a ratio of change in color difference in Test Example 1-1. The oxygen detecting device with the addition amount of 20 weight percent (inner filling amount: 15 weight percent) was particularly excellent. The oxygen detecting device with an addition amount of 30 weight percent (inner filling amount: 22 weight percent) and the oxygen detecting device with an addition amount of 50 weight percent (inner filling amount: 33 weight percent) were approximately identical to each other, as to both of which the difference from a blank was not observed after sixth day and thereafter.

FIG. 5 depicts a ratio of change in color difference in Test Example 1-2. The oxygen detecting device with an addition amount of 20 weight percent (inner filling amount: 15 weight percent) was excellent. An outstanding difference was not observed depending on the addition amount.

FIG. 6 depicts a ratio of change in color difference in Comparative Example 1-1. In particular, an oxygen detecting device with an addition amount of 20 weight percent (inner filling amount: 11 weight percent) had a significantly large change in color difference. This may be because silicic acid and calcium oxide, which are ingredients of silica, are present in a state of a mixture and there was an influence of calcium oxide.

Test Example 2

Subsequently, deoxidized preservation test with silica, i.e. the porous inorganic material, was performed.

In the testing of the Test Example 2, the oxygen detecting device obtained in the Test Example 1 was used. The device was preserved in a deoxidized state under an environment at 35 degrees Celsius. Under this preservation state, coloring was "red".

Then, every 15 days, the oxygen detecting device was exposed to air as a released state from the deoxidized preservation state so that its color was changed to "blue". Then, together with a deoxidizer ("Wonderkeep LP-100" (product name) from Powder Tech Corporation), 200 cc of air was injected in a nylon (registered trademark)/polyethylene bag and then the bag was sealed and left stand under an environment at 25 degrees Celsius.

The oxygen concentration in the bag in the sealed state after a lapse of approximately 6 hours was smaller than 0.1%.

With this state being taken as 0 hour, the period of time for changing the oxygen detecting device from "blue" to "red" was taken as a color-changing speed.

The standard value of this color-changing speed was assumed to be within 5 hours.

The results are depicted in "Table 4".

TABLE 4

|  |  | TEST EXAMPLE 2-1 | | | TEST EXAMPLE 2-2 | | | COMPARATIVE EXAMPLE 2-1 | | |
|---|---|---|---|---|---|---|---|---|---|---|
| TIME | BLANK | 15 wt % | 22 wt % | 33 wt % | 15 wt % | 23 wt % | 38 wt % | 11 wt % | 14 wt % | 28 wt % |
| 0-TH DAY | 4 | 4 | 4 | 4 | 4 | 4 | 4 | 4 | 4 | 4 |
| 15TH DAY | 5 | 4 | 4 | 4 | 5 | 5 | 5 | 5 | 5 | 5 |
| 30TH DAY | 8 | 4 | 4 | 4 | 6 | 6 | 5 | 5 | 5 | 5 |

From the results in Table 4, samples with the addition amounts of 20 weight percent, 30 weight percent, and 50 weight percent in Test Example 2-1 had a color-changing speed of 4 hours even after a lapse of 30 days, and their deterioration due to long preservation was not observed. On the other hand, samples in Test Example 2-2 and Comparative Example 2-1 had a color-changing speed of 5 hours to 6 hours after a lapse of 30 days.

INDUSTRIAL APPLICABILITY

As has been explained above, since the oxygen detecting device according to the present invention has excellent light resistance, it is excellent even if it is exposed to a fluorescent lamp for a long period of time in a display case that displays commercial products, and is suitable for use in quality check of the commercial products.

The invention claimed is:
1. An oxygen detector sheet comprising:
a sheet carrier having amorphous silica filled therein; and
an oxygen detecting fluid carried in the carrier,
wherein the content of the filled amorphous silica in the sheet carrier is 15 to 38 percent by weight.
2. An oxygen detecting device comprising:
a film having a predetermined oxygen transmittance; and
the oxygen detector sheet according to claim 1 covered and sealed with the film.
3. A method for manufacturing the oxygen detector sheet of claim 1, the method comprising:
producing a paper while adding amorphous silica thereto so that the amorphous silica is held in the paper at the filling ratio of 15 to 38 percent by weight, thereby form- ing a sheet carrier, the amorphous silica giving light resistance to the sheet carrier;

subsequently impregnating the sheet carrier with an oxygen detecting fluid; and drying the sheet carrier to obtain the oxygen detector sheet.

4. The oxygen detector sheet of claim 1, wherein the oxygen detecting fluid is an oxidation-reduction type.

* * * * *